US007754481B2

(12) United States Patent
Eberhardt et al.

(10) Patent No.: US 7,754,481 B2
(45) Date of Patent: Jul. 13, 2010

(54) KERATINOCYTES USEFUL FOR THE TREATMENT OF WOUNDS

(75) Inventors: Petra Eberhardt, Bad Schussenried (DE); Wolfgang Noe, San Diego, CA (US); Katharina Reif, Stadtbergen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 31 days.

(21) Appl. No.: 11/930,880

(22) Filed: Oct. 31, 2007

(65) Prior Publication Data
US 2008/0131967 A1 Jun. 5, 2008

Related U.S. Application Data

(62) Division of application No. 11/556,367, filed on Nov. 3, 2006, now Pat. No. 7,306,943, which is a division of application No. 10/268,496, filed on Oct. 10, 2002, now Pat. No. 7,247,478.

(51) Int. Cl.
*C12N 5/00* (2006.01)
*C12N 11/00* (2006.01)
(52) U.S. Cl. .................. 435/374; 435/371; 435/325; 435/366; 424/93.7
(58) Field of Classification Search ................ None
See application file for complete search history.

(56) References Cited

U.S. PATENT DOCUMENTS

| | | | |
|---|---|---|---|
| 4,016,036 A | 4/1977 | Green et al. | |
| 5,292,655 A | 3/1994 | Wille, Jr. | |
| 5,298,417 A | 3/1994 | Cancedda et al. | |
| 5,658,331 A | 8/1997 | Della Valle et al. | |
| 5,693,332 A | 12/1997 | Hansbrough | |
| 5,891,617 A | 4/1999 | Watson et al. | |
| 6,485,971 B1 | 11/2002 | Kaur et al. | |
| 6,585,969 B1 | 7/2003 | Van Bossuyt | |

FOREIGN PATENT DOCUMENTS

| | | |
|---|---|---|
| DE | 19917532 A1 | 10/2000 |
| EP | 02/96475 A1 | 12/1988 |
| EP | 0462426 A1 | 12/1991 |
| WO | 95/07611 A1 | 3/1995 |
| WO | 9624018 | 8/1996 |
| WO | 9310217 | 5/1999 |
| WO | 9947644 | 9/1999 |

OTHER PUBLICATIONS

Teepe, et al; Randomized Trial Comparing Cryopreserved Cultured Epidermal Allografts with Hydrocolloid Dressings in Healing Chronic Venous Ulcers; Journal of the American Academy of Dermatology; 1993; vol. 29; No. 6; pp. 982-988.
Maier, K., Transplantation von in-vitro-Epidermis-Chancen und Risiken; Quintessenz 3; pp. 289-304.
Pellegrini, et al; Location and Clonal Analysis of Stem Cells and Their Differentiated Progeny in the Human Ocular Surface; Journal of Cell Biology; vol. 145; No. 4; May 17, 1999; pp. 769-782; The Rockefeller University Press.
Pellegrini, et al; p63 Identifies Keratinocyte Stem Cells; Laboratory of Tissue Engineering IDI; Mar. 13, 2001; vol. 98; No. 6; pp. 3156-3161; PNAS.
Pellegrini, et al; Cultivation of Human Keratinocyte Stem Cells: Current and Future Clinical Applications; Medical Biological Engineering & Computing; 1998; vol. 36; pp. 778-790; Laboratory of Tissue Engineering I.D.C.
Harle-Bachor, et al; Telomerase Activity in the Regenerative Basal Layer of the Epidermis in Human Skin and in Immortal and Carcinoma-Derived Skin Keratinocytes; Cell Biology; Jun. 1996; vol. 93; pp. 6476-6481; Proc. Natl. Acad. Science USA.
Weaver, et al; Partial Trisomies in two Spontaneously Arising Long-Lived Human Keratinocyte Lines; in Vitro Cell Dev. Biology; Aug. 1991; vol. 27A; pp. 670-675; Tissue Culture Association.
Boukamp, et al; Normal Keratinization in a Spontaneously Immortalized Aneuploid Human Keratinocyte Cell Line; The Journal of Cell Biology; Mar. 1988; vol. 106; pp. 761-771; The Rockefeller University Press.
International Search Report Reference #PCT/EP 02/11459.
Maier, K., Transplantation von in-vitro-Epidermis-Chancen und Risiken; Quintessenz 3; pp. 289-304, (1993 ).
International Search Report Reference #PCT/EP 02/11459, Sep. 10, 2003.
Beele, et al; Repeated Cultured Epidermal Allografts in the Treatment of Chronic Leg Ulcers of Various Origins; Dermatologica; vol. 183 (1); pp. 31-35, (1991).
De Luca, et al; Treatment of Leg Ulcers With Cryopreserved Allogeneic Cultured Epithelium; A Multicenter Study; Archives of Dermatology; vol. 128 (5); May 1992; pp. 633-638.
Falanga, et al; Rapid Healing of Venous Ulcers and Lack of Clinical Rejection With an Allogeneic Cultured Human Skin Equivalent; Archives of Dermatology; vol. 134; 1998; pp. 293-300.
Harris, et al; Use of Hyaluronic Acid and Cultured Autologous Keratinocytes and Fibroblasts in Extensive Burns; Lancet; Jan. 2, 1999; vol. 353; pp. 35-36.
Lam, et al; Development and Evaluation of a New Composite Laserskin Graft; Journal of Trauma: Injury, Infection and Critical Care; 1999; vol. 47; pp. 918-922.
Lang, et al; Rapid Normalization of Epidermal Integrin Expression after Allografting of Human Keratinocytes; Journal of Investigative Dermatology; 1996; vol. 107; pp. 423-427.
Leigh, et al; Clinical Practice and Biological Effects of Keratinocyte Grafting; Annals of the Academy of Medicine; Jul. 1991; vol. 20 (4).
Lindgren, et al; Treatment of Venous Leg Ulcers with Cryopreserved Cultured Allogeneic Keratinocytes; A Prospective Open Controlled Study; British Journal of Dermatology; 1998; vol. 139 (2); pp. 271-275.

(Continued)

*Primary Examiner*—Jon P Weber
*Assistant Examiner*—Laura Schuberg
(74) *Attorney, Agent, or Firm*—Michael P. Morris; Mary-Ellen M. Devlin; Philip I. Datlow

(57) ABSTRACT

The invention relates to new keratinocytes which may be cultured in vitro and the advantageous use thereof for preparing a product which can be used to treat acute and chronic wounds.

3 Claims, 4 Drawing Sheets

OTHER PUBLICATIONS

Phillips; et al; Cultured Allogenic Keratinocyte Grafts in the Management of Wound Healing: Prognostic Factors; Journal of Dermatologic Surgery and Oncology; Nov. 1989; vol. 15 (11); pp. 1169-1176.

Schoenfeld, et al; Keratinozyten aus der Zellkultur sur Therapie von Hautdefekten; Hautarzt; 1993; vol. 44; pp. 281-289.

Tanczos, E.; Keratinozytentransplantation and Tissue Engineering. Neue Ansatze in der Behandlung chronischer Wunden; Zentralbl Chir; 124; Supp 1; 1999; pp. 81-86.

Determining the relative telomerase activity

| Cell Strain (Passage) | Telomerase Activity in % |
|---|---|
| HeLa | 100,00 |
| KC-BI-1 (1) | 1,96 |
| KC-BI-1 (12) | 0,08 |
| KC-BI-1 (18) | 0,68 |
| KC-BI-1 (40) | 1,96 |
| KC-BI-1 (57) | 1,08 |

Figure 3

Morphology of the keratinocytes KC-B1-1 after passages 5 and 60

Cell passage 60
300 Days

Cell passage 5
25 Days

KERATINOCYTES USEFUL FOR THE TREATMENT OF WOUNDS

CROSS-REFERENCE TO RELATED APPLICATIONS

This application is a division of U.S. application Ser. No. 11/556,367, filed Nov. 3, 2006 now U.S. Pat. No. 7,306,943, which is a division of U.S. application Ser. No. 10/268,496, filed Oct. 10, 2002 now U.S. Pat No 7,247,478.

FIELD OF THE INVENTION

The invention relates to new keratinocytes which may be cultivated in vitro and their beneficial use for preparing a product which can be used to treat acute and chronic wounds. The invention was thus made in the field of medicine, specifically in the field of wound healing by tissue engineering.

PRIOR ART

Allogeneic keratinocytes have successfully been used for quite a long time for the treatment of wounds, particularly ulcers and/or burns (Maier, 1993; Schönfeld et al., 1993). Wounds which prove resistant to treatment by conventional methods over lengthy periods can often be successfully treated using allogeneic keratinocytes (Phillips and Gilchrest, 1993; Beele et al., 1991; Leigh et al., 1991; Lindgren et al, 1998). To begin with, when using allogeneic keratinocytes, attention was directed predominantly to skin replacement, i.e. the regeneration of the transplanted epidermis. However, it was soon apparent that the success of the treatment is primarily based on the stimulation of the body's own re-epithelialisation and not on "growing" the allogeneic cell transplant in the wound. Recently, numerous investigations have shown that the transplanted keratinocytes remain in the wound for only a certain length of time and are then eliminated from the body in a manner which is clinically invisible (Kawai et al., 1993). The stimulation of the body's own wound healing is thus primarily brought about by an optimum release, in space and time, of a plurality of different growth factors, cytokines, extracellular matrix (ECM), smaller molecules and proteases by the allogeneic keratinocytes (Lang et al., 1996; Marcusson et al., 1992). The complexity and number of factors released confirms the therapeutic advantage over conventional single therapies, e.g. with isolated growth factors. Apart from the main effect of re-epithelialisation, however, treatment with keratinocytes also produces macroscopically and microscopically detectable changes in the granulation tissue (Lang et al., 1996). Another frequently described effect of keratinocytes which is beneficial to the patient is the marked analgesia after transplantation (Schönfeld et al., 1993).

For wound healing it is advantageous to use undifferentiated, actively dividing keratinocytes, as actively dividing keratinocytes appear to have a complex secretion profile which promotes wound healing. With the exception of the stem cells, undifferentiated keratinocytes lose their proliferation potential in vivo in the course of natural differentiation after only a few cell divisions, a process which has hitherto always been observed in the in vitro cultivation of keratinocytes (Barrandon and Green, 1987). Consequently, the actively dividing keratinocytes which are particularly suitable for wound healing have hitherto only been cultivated in vitro, which makes them difficult and expensive to use for medical purposes.

The allogeneic keratinocytes are used therapeutically either directly in the form of so-called "keratinocyte sheets", consisting of a multilayer, enzymatically detached cell aggregate, or together with biocompatible carriers under the title "biologically active wound healing dressings". The latter has the advantage that the cells do not require enzymatic pretreatment, detaching them from the substrate of the culture dish before they are used. Moreover, the use of biocompatible membranes as carriers for cultivating the keratinocytes (EP 0 462 462, U.S. Pat. Nos. 5,658,331; 5,693,332; EP 0518 920) makes it possible to prepare the biologically active wound healing dressings earlier, as the cells no longer have to form a self-contained cell aggregate. Carriers which have already grown subconfluent may be used for the wound treatment. Apart from being available sooner, the use of subconfluent cell aggregates has the additional advantage that correspondingly cultured keratinocytes are less sharply differentiated and are thus advantageous for treating wounds.

Keratinocytes may be cryopreserved for wound healing, without any harmful effects, directly or in conjunction with biocompatible carrier materials at temperatures between $-30$ and $-196°$ C., but preferably between $-70$ and $-90°$ C. (De Luca et al., 1992; Teepe et al., 1993). This further improves their therapeutic usefulness, as it is possible to some extent to keep a supply of biologically active wound healing dressings.

Problem of the Invention

The keratinocytes known from the prior art and biologically active wound healing dressings produced from them have certain drawbacks which the present invention set out to overcome.

An obvious disadvantage of the keratinocytes of primary origin known hitherto is that the said cells can only replicate themselves for a few generations of cells by means of in vitro cell culture processes without losing their high rate of division and hence their suitability for the preparation of biologically active wound healing dressings. According to the prior art the skilled man is only able to increase the number of cells by a factor of about $10^3$ to $10^4$ by in vitro cultivation (Tanczos et al., 1999).

Another disadvantage which flows from this is the fact that the limited culturability of said keratinocytes in vitro makes it essential to carry out frequent and complex re-isolation; this in turn means that the replicated cell material obtained is not uniform and hence the wound healing dressings produced therefrom will, or at least may, in all probability have differences in quality.

A further disadvantage is that the re-isolation of the keratinocytes from various donors constitutes an increased risk of infection to the recipient of the wound healing aggregate. An increased risk of HIV or hepatitis might arise, for example.

DESCRIPTION OF THE INVENTION

The invention relates to keratinocytes with a high proliferation potential, which are not immortalised and which can be replicated at least 150 times by in vitro cell culture methods. This results in a cell multiplication factor of about $10^{44}$. The corresponding keratinocytes still retain their advantageous properties for the treatment of wounds.

The keratinocytes according to the invention are primarily keratinocytes isolated from a donor and culturable in vitro, while the isolation and initial cultivation may be carried out by anyone skilled in the art, according to the process described by Rheinwald and Green in 1975, for example.

The invention preferably relates to keratinocytes which are isolated from the epidermal part of a foreskin. Keratinocytes of human origin, particularly keratinocytes of the culture KC-BI-1, which were deposited on 27 Jun. 2001 at the DSMZ-Deutsche Sammlung von Mikroorganismen und Zellkulturen [German Collection of Microorganisms and Cell Cultures] GmbH, Braunschweig, Germany under Accession Number DSM ACC2514 for the purposes of patent proceedings according to the Budapest Agreement, are preferred. The invention also covers keratinocytes which are derived from the culture KC-BI-1 (DSM ACC2514). Thus, the invention also relates to all cells and cultures which are and/or may be generated by subpassaging and/or subcloning the original culture KC-BI-1.

The cultivation of the keratinocytes according to the invention is described by way of example in relation to the keratinocytes KC-BI-1 (Example 1). The use of the complex medium specified in Example 1 and the use of feeder cells, preferably the use of lethally irradiated murine 3T3 fibroblasts, is advantageous for the culturing. The amount of foetal calf serum should be between 2 and 10%. The preparation of the feeder cells is known to those skilled in the art and may be carried out for example by the process described in Example 2. Subcultivation of the keratinocytes according to the invention at a maximum confluence of 80% is particularly advantageous. The keratinocytes may be cultured at 35 to 38° C., preferably at 37° C., at a relative humidity of >90%, preferably 95% and a $CO_2$ saturation of 5 to 9%.

With the process described in Example 1 the population doubling time for the keratinocytes, particularly human keratinocytes from the epidermal part of a foreskin, is between 1 and 2 days (FIG. 1). The cells can be cultured over numerous passages at a substantially constant replication rate (FIG. 2). However, the present invention is not restricted to just the keratinocytes KC-BI-1, but rather it is possible for a skilled man to perform the invention under appropriate conditions with any keratinocytes that are not immortalised and may be doubled at least 150 times by in vitro cell culture methods, especially those:

that may be doubled at least 150 times by in vitro cell culture methods and are isolated from the epidermal parts of a foreskin;

that may be doubled at least 150 times by in vitro cell culture methods and which are cells from the culture KC-BI-1 (DSM ACC 2514), or keratinocytes derived therefrom;

that may be doubled at least 150 times by in vitro cell culture methods and which:

a) cannot be replicated in the absence of foetal calf serum and/or b) in the absence of feeder cells and/or c) in the absence of Epidermal Growth Factor (EGF);

that may be doubled at least 150 times by in vitro cell culture methods and which have little or no telomerase activity;

The expression "not immortalised" in relation to the present invention means that primarily isolated keratinocytes and the keratinocytes cultured here are not spontaneously transformed and/or have not been transformed by molecular-biological, chemical or physical methods known from the research. The latter means that the cells have not been treated either using e.g. viral factors or sequences, chemically mutagenic substances or, for example, by irradiation or a combination of different processes.

Keratinocytes which "are not immortalised" also means that compared with transformed tumour cell lines (Härle-Bachor and Boukamp, 1993) or compared with immortalised cell lines, preferably the cell line HeLa, the said keratinocytes have no telomerase activity or a substantially reduced telomerase activity (cf. FIG. 3). This is particularly true also in comparison with the immortalised keratinocyte cell line HaCat.

The expression "not immortalised" also means that said keratinocytes cannot be replicated in the absence of foetal calf serum and/or in the absence of feeder cells and/or in the absence of epidermal growth factor, EGF, as immortalised keratinocytes can, for example (Schoop et al., 1999).

The expression "not immortalised" also means, however, that said keratinocytes do not change their characteristic phenotype as the cell replication increases (cf. FIG. 4).

"Not immortalised" also means that the said keratinocytes exhibit a normal differentiation profile after transplantation onto nude mice, preferably BALB/c. "Normal differentiation potential" here means the ability of the keratinocytes to develop into terminally differentiated keratinocytes and form suprabasal epidermal layers as well as a stratum corneum in the same way as autologous keratinocytes.

The present invention also relates to keratinocytes which are not immortalised and which can be replicated at least 200 times by in vitro cell culture methods. The invention further relates to keratinocytes which are not immortalised and can be replicated at least 250 times by in vitro cell culture methods. The invention also relates to keratinocytes which are not immortalised and can be replicated at least 300 times by in vitro cell culture methods.

The present invention advantageously enables the said keratinocytes to be replicated from only one donor or only a few donors. Starting from one donation, for example, $10^{44}$ cells may be produced after 150 cell replications, $10^{77}$ cells after 250 cell replications and $10^{90}$ cells after 300 cell replications. Thus, the invention makes it possible for the first time to produce large quantities of standardised cell material for the preparation of biologically active wound healing aggregates of constant, verifiable quality. A corresponding amount of standardised cell material may be replicated, for example, starting from a cryopreserved cell bank, which is in turn produced from keratinocytes having the properties according to the invention.

By using standardised cell material as the starting material for preparing biologically active wound healing dressings the risk of infection to the possible recipients is also reduced, as the isolation of the keratinocytes is restricted to a few donors, preferably one donor.

Thus, the invention overcomes serious disadvantages which currently consist of the merely restricted passaging of the keratinocytes known hitherto.

The present invention further relates to a product which consists of a carrier coated with the keratinocytes according to the invention. "Coated" for the purposes of the invention means that the surface of the carrier is partially or totally colonised with the keratinocytes according to the invention. A partially colonised carrier is particularly suitable, as a shorter culture time is needed before the carrier can be used for wound treatment.

A suitable carrier for the purposes of the invention is characterised in that it is a biocompatible carrier material which may be used to prepare a pharmaceutical composition. Hydrophobic biocompatible carrier materials, as described in WO 91/13638, for example, may be used. However, it is also possible to use carrier materials with predominantly hydrophilic properties.

A preferred embodiment of the present invention comprises the use of carrier materials which consist of a polymer of esterified hyaluronic acid. In a particularly preferred embodiment a polymer of esterified hyaluronic acid is used, consisting of a perforated polymer film of a defined geometry.

The polymer film has a thickness of 10 to 500 µm, for example, and is perforated with holes measuring between 10 and 1000 µm, the holes being of a defined, constant size and forming ordered rows, separated from one another by a constant spacing of 50 to 1000 µm. A film of this kind is described in EP 0 462 426. Perforated carrier materials are particularly suitable as they do not require the biologically active wound dressing to be placed on the wound in any particular direction. Example 3 describes the preparation, by way of example, of a perforated carrier matrix of esterified hyaluronic acid of a defined geometry colonised by keratinocytes according to the invention. The carrier matrix is a product made by Messrs Fidia Advanced Biopolymers Ltd., Abano Terme, Italy, marketed in Germany under the product name "Laserskin".

The particularly preferred suitability of this carrier material for producing a biologically active wound dressing in conjunction with keratinocytes has already been demonstrated on an animal model (Lam et al., 1999) and in humans (Harris et al., 1999). Apart from improved migration and differentiation of the epithelial cells the matrix consisting of hyaluronic acid ester has a positive effect on angiogenesis and collagen production. The wound dressings currently used with hyaluronic acid ester as matrix are, however, coated with autologous keratinocytes and/or skin equivalents of complex structure obtained from keratinocytes and fibroblasts. They therefore suffer from the disadvantages of the prior art described above. These disadvantages may be overcome particularly by the use of the advantageous allogeneic keratinocytes according to the invention.

Another preferred embodiment of the invention relates to a product comprising the keratinocytes according to the invention together with reabsorbable polymers, consisting of polyesters, polycarbonates, polyanhydrides, polyorthoesters, polydepsipeptides, polyetheresters, polyamino acids or polyphosphazenes, especially poly(L-lactide), poly(D,L-lactide), poly(L-lactide-co-D,L-lactide), poly(glycolide), poly(L-lactide-co-glycolide), poly(L-lactide-co-trimethylene-carbonate) or poly(dioxanone). These polymers are both perforated and unperforated.

The present invention also relates to a method of cryopreserving the keratinocytes according to the invention at a temperature of −20° C. to −196° C., preferably at a temperature below −180° C. The said keratinocytes can be frozen by standardised methods familiar to anyone skilled in the art. DMSO, inter alia, may be used as the cryoprotectant. It is also possible to use other cryoprotectants such as glycerol, hydroxyethyl starch or a combination of the two, and a combination of these with DMSO. Suitable methods are described for example in WO 96/24018, U.S. Pat. Nos. 5,891,617 or 5,298,417.

The present invention also relates to the cryopreserving of the carriers coated with the keratinocytes according to the invention, characterised in that the keratinocytes with their corresponding carrier are cryopreserved at a temperature of −20° C. to −196° C., preferably at −60° C. to −80° C. The advantage of cryopreserving is that the product obtained in large quantities can be stored and thus examined for uniformity of quality by random sampling before clinical use. Finally, storage ensures that the wound healing aggregates are available at short notice for medical purposes.

A suitable cryoprotectant for the product according to the invention is hydroxyethyl starch, for example, in a concentration of 7-13% (w/w). However, it is also possible to use DMSO or glycerol as well as a combination of various cryoprotectants, particularly hydroxyethyl starch, DMSO and/or glycerol. It is also possible to use trehalose as cryoprotectant.

After a rapid reduction in temperature from 37° C. to −5 to −10° C., preferably −6 to −8° C. within 2-5 min, the product comprising carrier and keratinocytes according to the invention is equilibrated at the appropriate temperature for 15-30 min, preferably for 23-26 min. Then the product is cooled at a freezing rate of <1° C./min, preferably from 0.2 to 0.6° C./min, most preferably 0.4° C./min, to a temperature of e.g. −60 to −80° C.

Example 4 describes, by way of example, the cryopreserving of a carrier matrix of hyaluronic acid ester coated with KC-BI-1. However, it is also possible to use other methods of cryopreserving, e.g. the methods described in WO 95/707611, WO 96/24018, EP 0 296 475; this list should not be regarded as exhaustive but merely indicates that methods of cryopreserving products consisting of biocompatible carriers and keratinocytes are part of the current state of the art.

The present invention also relates to the medical use of the keratinocytes according to the invention described here and/or the product of said keratinocytes and a carrier described here, particularly to their use for treating wounds. One embodiment of the invention consists of the use of the keratinocytes according to the invention and/or the product of said keratinocytes and a carrier in the treatment of burns and/or ulcers. Burns which may be treated are preferably second degree burns while the ulcers are preferably chronic ulcers of the lower leg which are difficult to heal, of the type Ulcus cruris, preferably Ulcus cruris venosum or diabetic ulcers, and also decubital ulcers.

The medical use includes a combined and/or supplementary use of said keratinocytes and/or the product consisting of keratinocytes and carrier according to the invention with conventional therapies known in the art with a beneficial effect on wound healing. This means a combined and/or supplementary use of one or more other substance(s) with a beneficial effect on wound healing. Mention may be made of the supplementary and/or combined treatment of Ulcus cruris venosum with hydrocolloid dressings and/or the additional use of antimicrobial substances, e.g. the administering of antibiotics.

The invention also relates to the keratinocytes according to the invention and/or the product of a biocompatible carrier and said keratinocytes for preparing a medical product for treating wounds, particularly for treating burns and/or ulcers, e.g. for the treatment of second degree burns, Ulcus cruris (venosum), diabetic ulcers or decubital ulcers.

The invention further relates to a process for treating these wounds, this process being characterised in that the keratinocytes according to the invention and/or the product according to the invention comprising keratinocytes and carrier is or are placed on the wounds to be treated. The keratinocytes and the product may be used either fresh or after cryopreservation. A corresponding method of treating wounds is described in Example 5.

DESCRIPTION OF THE FIGURES

FIG. 3: Determining the relative telomerase activity. This shows the relative telomerase activity for the keratinocytes KC-BI-1 after passage 1, 12, 18, 40 and 57 compared with the activity of the cell line HeLa. The Figure shows almost no or only slight telomerase activity for the keratinocytes KC-BI-1 compared with the immortalised cell line HeLa.

EXEMPLIFYING EMBODIMENTS

Example 1

Figure 1:
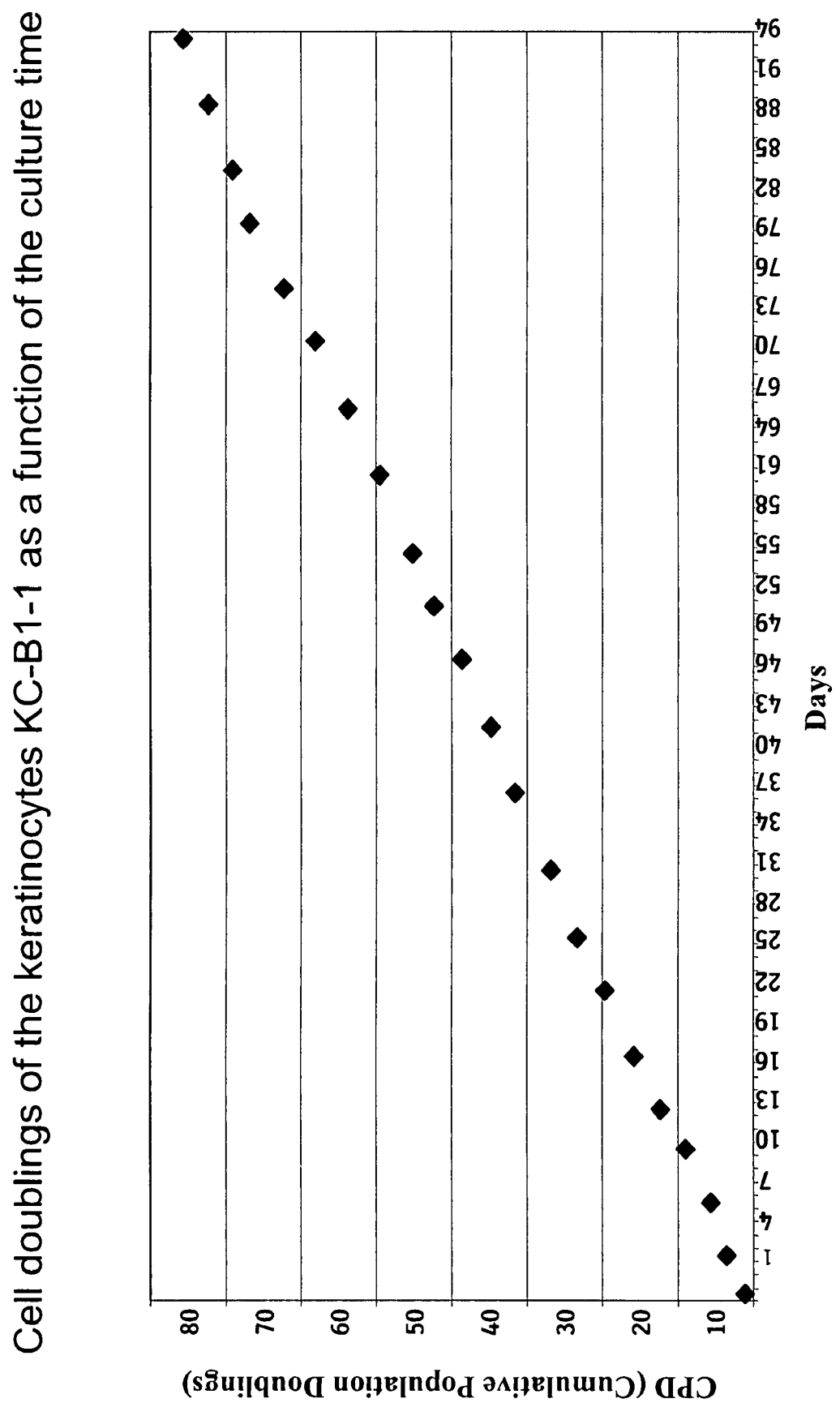
FIG. 1: Cell replication of the keratinocytes KC-BI-1 as a function of the culture time. This shows the number of cell replications (CPD=Cumulative Population Doublings) of the keratinocytes KC-BI-1 over a culture period of 94 days. Within the 94 day observation period the cells doubled roughly 75 times. This corresponds to a mean doubling time of 1.25 days per cell replication, or 12.5 per 10 days.
Figure 2:
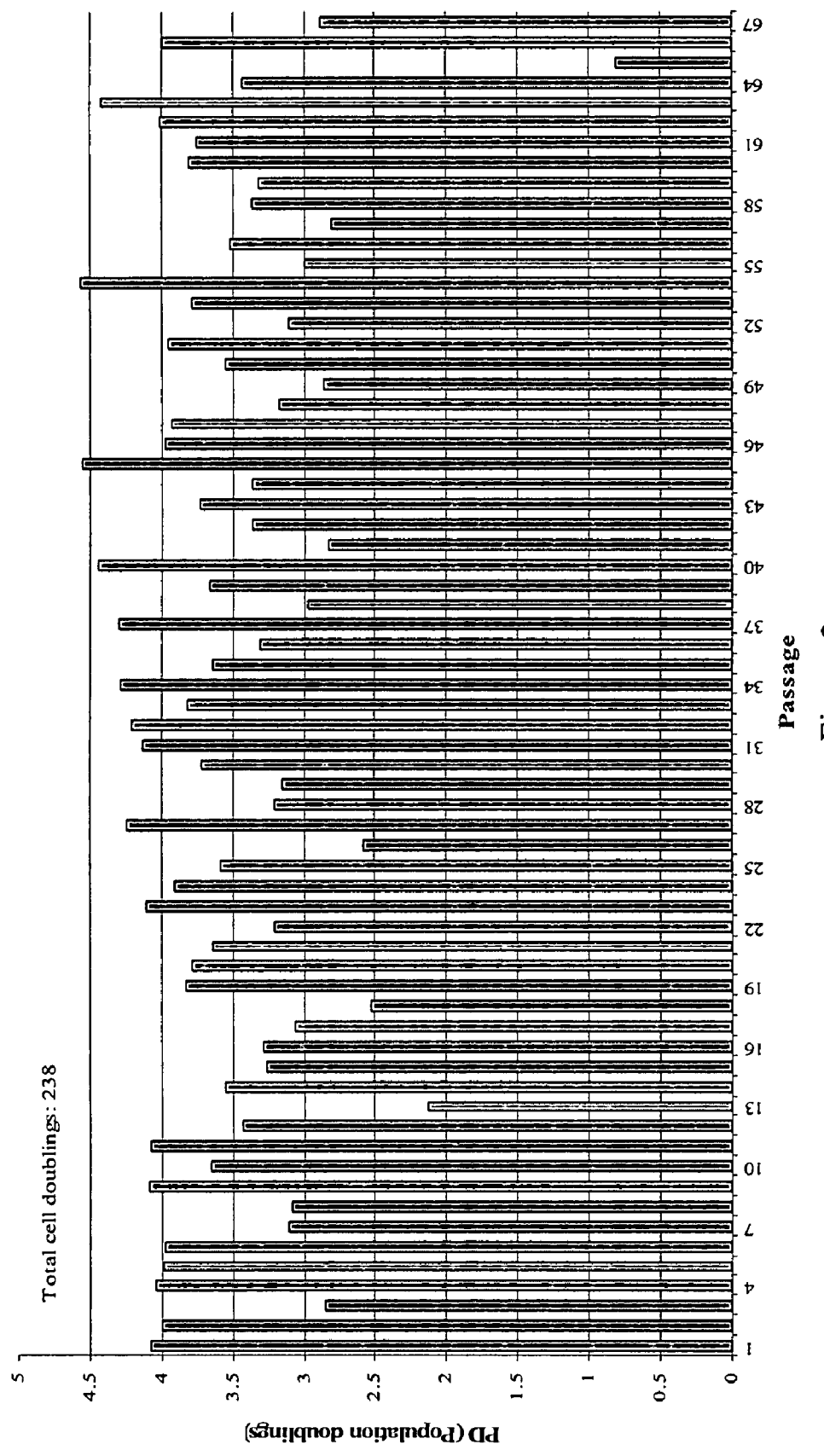
FIG. 2: Doubling of the keratinocytes KC-BI-1 over a period of 10 months. This shows the cell replication of the keratinocytes KC-BI-1 over 10 months, given as population doublings (PD) as a function of the cell passages 1-67.
Figure 4:
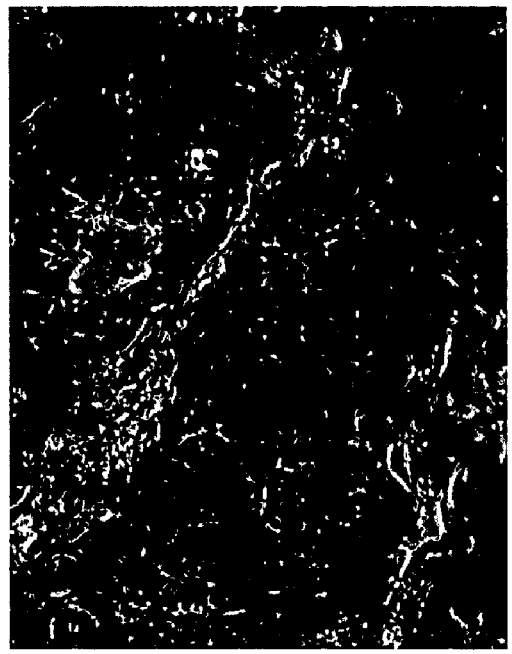
FIG. 4: Morphology of the keratinocytes KC-BI-1 after passages 5 and 60. Viewed under the optical microscope the keratinocytes KC-BI-1 do not exhibit any morphological differences between cell passage 5 (culture time 25 days) and cell passage 60 (culture time 300 days).
Figure 4:

Process for Culturing the Keratinocytes According to the Invention Taking the Culture KC-BI-1 (DSM ACC2514) as an Example 1. Material Keratinocytes KC-BI-1; irradiated 3T3-murine fibroblasts (feeder cells, for preparation cf. Example 2); cell culture medium K/1 (for composition see below); EDTA (0.02%); trypsin/EDTA (0.05%/0.01%); cell culture flasks (T-flask): 25 cm$^2$, 80 cm$^2$, 175 cm$^2$ 2. Thawing the Cells 2.1 Thawing the Feeder Cells The cells are rapidly thawed and placed in 5-10 ml of preheated K/1 medium. A corresponding quantity of feeder cells are transferred into a suitable cell culture flask and topped up with K/1 medium:

| | | |
|---|---|---|
| 25 cm$^2$ T-flask | 0.5 × 10$^6$ cells | Final volume of medium: 5-6 ml |
| 80 cm$^2$ T-flask | 1.5 × 10$^6$ cells | Final volume of medium: 20 ml |
| 175 cm$^2$ T-flask | 3.5 × 10$^6$ cells | Final volume of medium: 50 ml |

The feeder cells may be used immediately or within 24 hours.

2.2 Thawing the Keratinocytes

The cells are rapidly thawed and placed in 5-10 ml of preheated K/1 medium. A corresponding quantity of cells are added to the cell culture flasks already containing feeder cells and topped up with fresh medium:

| | | |
|---|---|---|
| 25 cm$^2$ T-flask | 0.15 × 10$^6$ cells; | Final volume of medium: 6-10 mL |
| 80 cm$^2$ T-flask | 0.4 × 10$^6$ cells; | Final volume of medium: 20 mL |
| 175 cm$^2$ T-flask | 1 × 10$^6$ cells; | Final volume of medium: 50 mL |

3.0 Cultivation

The cells are incubated at 35-39° C., preferably at 37° C. The relative humidity is >90%, preferably 95% and the $CO_2$ concentration is 5-9%. The keratinocytes are subcultured at a maximum confluence of 80%.

For this, the cell culture supernatant is discarded. The feeder cells are rinsed twice with 0.02% EDTA (2-10 ml) and incubated for 5-10 min at 37° C., then detached from the cell culture flask by tapping it (or shaking it). The keratinocytes are then treated with trypsin/EDTA (0.05%/0.01%, 1-6 ml) for 5-10 min at 37° C. and carefully detached by tapping. If necessary the remaining cells are carefully scraped off using a cell spatula. The trypsin/EDTA solution is neutralised by the addition of K/1 medium and the cells are separated by careful pipetting up and down. The cells are seeded out in the cell numbers specified in 2.2. The cell culture medium K/1 is changed on day 3 and then every two days.

4.0 Preparation of the K/1 Medium

All the components and the stock solutions are combined one after another in the sequence given in Table 1. The mixture is made up to 1 liter with WFI (water for injection). Then the pH is adjusted to 7.0 to 7.2 with NaOH or HCl. The osmolarity should be between 320-400 mOsm/kg. Finally, the medium K/1 is sterile-filtered.

4.1 Preparation of the Stock Solutions

Triiodothyronine 13.6 mg of triiodothyronine are dissolved in 1 ml of 0.1 NaOH and 99 ml of PBS are added thereto. The finished solution is diluted 1:100 in PBS. 1 ml of this solution is required per liter of medium.

EGF 1 mg of EGF is dissolved in 100 ml of WFI. 1 ml of this solution is required per liter of medium.

rh-Insulin (only soluble at pH<4.0)

5 g of rh-insulin are added to 0.9 L of WFI and the pH is adjusted to 2.5 with 6M HCl. After the rh-insulin has dissolved, the pH is adjusted to 8.0 with 1M NaOH. The mixture is made up to 1 liter with WFI. 1 ml of this solution is required per liter of medium.

| 4.2 Composition of the medium | |
|---|---|
| components | concentration/L |
| WFI (water for injection) | 0.8 L |
| DMEM with glutamine | 10.035 g |
| HAM's F12 | 2.66 g |
| sodium hydrogen carbonate | 3.07 g |
| Na-pyruvate | 0.11 g |
| Apo-Transferrin | 5 mg |
| Adenine-Hemisulphate | 147.4 mg |
| Forskolin (soluble in a few drops of DMSO) | 2.05 mg |
| Rh-Insulin-Concentrate | 1.0 mL |
| Hydrocortisone 10 mM | 0.11 mL |
| triiodothyronine stock solution | 1.0 mL |
| EGF-stock solution | 1.0 mL |
| Phenol red | 8.1 mg |
| FCS (2-10%) | 20-100 mL |
| 6M HCl | as required |
| 40% NaOH | as required |
| WFI | add to 1.0 L |

However, the cells may also be cultured from fresh biopsy material, e.g. from the epidermal part of a foreskin. The primary isolation of the undifferentiated, proliferating keratinocytes may be carried out using the method described by Rheinwald and Green in 1975.

The feeder cells used may be, for example, the cells described in Example 2. It is also conceivable to use other lethal fibroblasts, preferably other murine fibroblasts, most preferably descendants of cell line 3T3.

Example 2

Preparation of Irradiated 3T3 Feeder Cells for Cultivating Keratinocytes

1. Material

Murine 3T3 fibroblasts (e.g. ATCC CCL 92, 3T3-Swiss albino, contact-inhibited fibroblasts) which may be obtained from the American Type Culture Collection (ATCC), 10801 University Boulevard, Manassas, Va., USA, DMEM+10% foetal calf serum (FCS); PBS; 0.2% trypsin solution; 0.04% EDTA solution; cell culture flasks (T-flasks): 25 cm$^2$, 80 cm$^2$, 175 cm$^2$ 2. Thawing the Cells The cells are rapidly thawed and added to 5-10 ml of preheated medium. DMSO-containing medium is removed after centrifugation. The cells are suspended in 5-10 ml of medium. After the cell number has been determined the cells are seeded into suitable cell culture flasks in a density of $10^3$ to $10^4$ cells/cm$^2$. They are incubated at 35-39° C., preferably at 37° C. The relative humidity is >90%, preferably 95% and the $CO_2$ concentration is 5-9%.

3. Culturing the Cells

The cells are inspected daily for growth. The cell density should not exceed a maximum confluence of 70-80%. Subculturing is carried out, as necessary, every 2 to 4 days. For this, the medium is discarded and the cells are washed with a suitable amount of a 1:2 mixture of EDTA and trypsin (0.5-5 ml). Then the cells detached are taken up in 3.5-20 ml of medium. The cells are re-seeded at a density of $10^3$ to $10^4$ cells/cm$^2$.

4. Irradiation of the Feeder Cells

The feeder cells are irradiated with a dose of about 60 Gy (6000 rad in a $^{137}$Cs source).

Both the irradiated and the non-irradiated cells can be cryopreserved in liquid nitrogen using standard methods and stored for long periods.

Example 3

Method of Coating a Carrier Matrix, in this Case Laserskin, with Keratinocytes from the Culture KC-BI-1 (DSM ACC2514)

The preparation of the biologically active wound healing dressing according to the invention will now be described by way of example. The wound healing dressing described here consists of the keratinocytes KC-BI-1 according to the invention and Laserskin, a bioreabsorbable carrier matrix of hyaluronic acid ester.

However, the invention is not restricted to the combination described here. Rather, any keratinocytes of the following description may be used for the coating:

Keratinocytes that are not immortalised and may be doubled at least 150 times by in vitro cell culture methods, especially those:

that may be doubled at least 150 times by in vitro cell culture methods and are isolated from the epidermal parts of a foreskin;

that may be doubled at least 150 times by in vitro cell culture methods and which are cells from the culture KC-BI-1 (DSM ACC 2514), or keratinocytes derived therefrom;

that may be doubled at least 150 times by in vitro cell culture methods and which:

a) cannot be replicated in the absence of foetal calf serum and/or b) in the absence of feeder cells and/or c) in the absence of Epidermal Growth Factor (EGF);

that may be doubled at least 150 times by in vitro cell culture methods and which have little or no telomerase activity;

that may be doubled at least 150 times by in vitro cell culture methods and which can be replicated at least 200 times by in vitro cell culture methods;

that may be doubled at least 150 times by in vitro cell culture methods and which can be replicated at least 250 times by in vitro cell culture methods; and that can be replicated at least 300 times by in vitro cell culture methods.

It is also possible to use other suitable carrier matrices, provided that they are biocompatible carrier materials which may be used to prepare a pharmaceutical composition. For example, hydrophobic biocompatible carrier materials as described in WO 91/13638 may be used. In addition, however, it is also possible to use carrier materials with predominantly hydrophilic properties.

Another preferred embodiment of the invention comprises using the keratinocytes according to the invention together with reabsorbable polymers, consisting of polyesters, polycarbonates, polyanhydrides, polyorthoesters, polydepsipeptides, polyetheresters, polyamino acids or polyphosphazenes, especially poly(L-lactide), poly(D,L-lactide), poly(L-lactide-co-D,L-lactide), poly(glycolide), poly(L-lactide-co-glycolide), poly(L-lactide-co-trimethylene-carbonate) or poly (dioxanone), and using perforated films consisting of said polymers.

1. Material

K/1 medium (cf. Example 1); PBS, 0.04% EDTA (diluted to 0.02% with PBS); trypsin/EDTA (0.05%/0.01%); sterile Roux dishes (T 25 cm$^2$, T 80 cm$^2$, T 175 cm$^2$), Laserskin (Messrs. Fidia Advanced Biopolymers srl, Abano Terme, Italy) in 144×21 Petri dishes (145 cm$^2$ surface area); 3T3 feeder cells; keratinocytes according to the invention such as KC-BI-1 for example 2. Culturing the Biologically Active Wound Healing Dressing 2.1. Material Irradiated feeder cells, e.g. the murine 3T3 fibroblasts mentioned in Example 2; keratinocytes according to the invention from stock; 8.5 cm×8.5 cm pieces of Laserskin in a Petri dish (finished product); K/2 medium 2.2. Seeding Out the 3T3 Feeder Cells The feeder cells, prepared according to Example 2, are placed on Laserskin in a seeding density of about 15,000 to 25,000 cells/cm$^2$ (roughly corresponding to 3×10$^6$ cells/Petri dish). The Petri dish is then incubated at 35 to 37° C. at >90% relative humidity and 5-11% $CO_2$, preferably 7-9%, in an incubator at 37° C. The keratinocytes are seeded onto the feeder cell lawn either on the same day or, at the latest, the next day (after 24 hours).

2.3. Seeding Out and Culturing the Keratinocytes

The biologically active wound healing dressings are prepared with the keratinocytes according to the invention. The subculturing of the keratinocytes may, for example, be carried out as follows:

The subconfluent cultures are rinsed once with 0.02% EDTA (80 cm$^2$ Roux dish: 8 mL; 175 cm$^2$ Roux dish: 10 ml). Then the feeder cells are incubated with 0.02% EDTA for 5-10 min at 37° C. (80 cm² Roux dish: 8 mL; 175 cm² Roux dish: 10 ml) and detached by shaking carefully.

The keratinocytes are dissolved as in Example 1 with a trypsin/EDTA mixture (0.05%/0.01%) (80 cm² Roux dish: 2-3 mL; 175 cm² Roux dish: 5-6 ml), then taken up in cell culture medium (80 cm Roux dish: 7-8 mL; 175 cm Roux dish: 14-15 ml) and separated by carefully pipetting up and down.

The keratinocytes according to the invention are applied to the Laserskin film provided with feeder cells, in a seeding density of about 15,000 to 25,000 cells/cm² (roughly corresponding to $3\times10^6$ cells/Petri dish). Then the cells are incubated until 30-100% confluent, preferably 80-100% confluent, at 35-39° C., preferably at 37° C. The relative humidity is >90%, preferably 95% and the $CO_2$ concentration is 5-9%.

Example 4

Method of Cryopreserving the Biologically Active Wound Healing Dressing According to the Invention After the keratinocytes have colonised the carrier matrix to a confluence of 30-100% preferably 80-100%, the product according to the invention may be frozen in suitable containers, e.g. heat-sealable PP bags, under controlled conditions. To do this, culture medium is carefully removed and replaced by 20 ml of K/2 freezing medium at a temperature of 2-6° C. The product is then packaged under sterile conditions and frozen according to the following procedure:

After a rapid lowering of the temperature to −5 to −10° C., preferably −6 to −8° C. within 2-5 min, the product is equilibrated at the corresponding temperature for 15-30 min, preferably for 23-25 min. Then the product is cooled to a temperature of, for example, −60 to −80° C. at a freezing rate of <1° C./min, preferably 0.2 to 0.6° C./min, most preferably 0.4° C./min. The product is stored at −60 to −80° C.

K/2 Freezing Medium

K/1 Growth Medium (cf. Example 1) mixed with 7-13% (w/w) of hydroxyethyl starch.

Example 5

Example of the Use of a Carrier Matrix Colonised with the Keratinocytes According to the Invention for Covering Wounds, Taking Venous Leg Ulcers as an Example 1. Transporting Freshly Prepared Wound Healing Dressings After the keratinocytes have grown to 30-100%, preferably 80-100% confluence on the Laserskin, the culture is rinsed one or more times with a suitable quantity, preferably 30 ml, of K/3 transporting medium. The biologically active wound healing dressing is transported in a suitable amount, preferably in 20 ml, of K/3 transporting medium. The headroom of the Petri dish is briefly gassed with an air mixture of 5-10% $CO_2$, sealed with adhesive tape, e.g. Parafilm, and immediately delivered to the clinic in a transportation box.

K/3 Transporting Medium:

Growth medium K/1 (cf. Example 1) without foetal calf serum (FCS). However, it is also possible to use simple physiological saline solutions e.g. based on phosphate-borate, e.g. PBS, or based on HEPES (N-2-hydroxyethylpiperazin-N'-2-ethanesulphonic acid) or MES ([2-N-morpholino]ethanesulphonic acid).

2. Transporting Cryopreserved Wound Healing Dressings

Cryopreserved wound healing dressings may typically be supplied to the clinics on dry ice. However, other forms of transportation are possible, provided that the wound healing dressings are transported at a temperature below −60° C.

The cryopreserved wound healing dressings are rapidly thawed. Then the freezing medium is removed and the dressing is rinsed one or more times with K/3 transporting medium (see above) or another suitable physiological solution such as Ringer's solution, for example.

3. Therapeutic Use

The dressing is then placed on the wound. When non-perforated carrier materials are used, the wound healing dressing has to be positioned correctly with the cells facing the wound. The use of perforated carriers which allow keratinocytes to colonise both sides of the carrier (e.g. Laserskin) means that the wound healing dressing according to the invention does not have to be placed on the wound being treated in any particular direction. Depending on the success of the therapy the treatment may be repeated a number of times.

Example 6

Genetic Characterisation of the Keratinocyte Cell KC-BI-1 (DSM ACC2514)

KC-BI-1 cells were subcultured over a number of passages using the method according to the invention described above. Cells from passage 4, 13 and 121 were then subjected to genetic analysis, investigating the length polymorphism of 15 different loci (CSF1P0, D13S317, D16S539, D18S51, D21S11, D3S1358, D5S818, D7S820, D8S1179, FGA, Penta D, Penta E, TH01, TPOX and vWA). Analysis was carried out using a method known in the art. For this, the corresponding alleles were amplified using a test to determine paternity (PoewerPlex® 16 System) produced by Messrs Promega (Mannheim, Germany), according to the manufacturer's instructions. The alleles may be identified by determining the fragment length (length standard ILS 600 is part of the above kit). Data on allele frequencies in the population can be found in the corresponding Tables.

Analysis has shown agreement of all the alleles at all the loci for all the cell passages analysed. The data thus enable the KC-BI-1 cells to be genetically classified. A classification probability of >99.999% was determined from the allele frequencies.

Determining the DNA length polymorphism:

| Marker | Donor | KC-BI-1 Passage 4 | KC-BI-1 Passage 13 | KC-BI-1 Passage 121 |
|---|---|---|---|---|
| CSF1PO | 11 | 11 | 11 | 11 |
|  | 12 | 12 | 12 | 12 |
| D13S317 | 8 | 8 | 8 | 8 |
|  | 13 | 13 | 13 | 13 |
| D16S539 | 11 | 11 | 11 | 11 |
|  | 13 | 13 | 13 | 13 |
| D18S51 | 13 | 13 | 13 | 13 |
|  | 17 | 17 | 17 | 17 |
| D21S11 | 29 | 29 | 29 | 29 |
|  | 29 | 29 | 29 | 29 |
| D3S1358 | 15 | 15 | 15 | 15 |
|  | 15 | 15 | 15 | 15 |
| D5S818 | 9 | 9 | 9 | 9 |
|  | 11 | 11 | 11 | 11 |
| D7S820 | 9 | 9 | 9 | 9 |

-continued

| Marker | Donor | KC-BI-1 Passage 4 | KC-BI-1 Passage 13 | KC-BI-1 Passage 121 |
|---|---|---|---|---|
|  | 9 | 9 | 9 | 9 |
| D8S1179 | 10 | 10 | 10 | 10 |
|  | 14 | 14 | 14 | 14 |
| FGA | 23 | 23 | 23 | 23 |
|  | 26 | 26 | 26 | 26 |
| Penta D | 11 | 11 | 11 | 11 |
|  | 12 | 12 | 12 | 12 |
| Penta E | 10 | 10 | 10 | 10 |
|  | 12 | 12 | 12 | 12 |
| TH01 | 8 | 8 | 8 | 8 |
|  | 9.3 | 9.3 | 9.3 | 9.3 |
| TPOX | 8 | 8 | 8 | 8 |
|  | 10 | 10 | 10 | 10 |
| vWA | 16 | 16 | 16 | 16 |
|  | 18 | 18 | 18 | 18 |

LITERATURE

Beele H; Naeyaert J M; Goeteyn M; De Mil M; Kint A (1991): Repeated cultured epidermal allografts in the treatment of chronic leg ulcers of various origins. Dermatologica, 183 (1) 31-5.

De Luca M; Albanese E; Cancedda R; Viacava A; Faggioni A; Zambruno G; Giannetti A (1992): Treatment of leg ulcers with cryopreserved allogeneic cultured epithelium. A multicenter study. Archives of Dermatology, 128 (5) 633-8.

Härle-Bachor C; Boukamp P (1993) Telomerase activity in the regenerative basal layer of the epidermis in human skin and in immortal and carcinoma-derived skin keratinocytes. PNAS 93; 6476-6481

Falanga V et al. (1998): Rapid Healing of venous ulcers and lack of clinical rejection with an allogeneic cultured human skin equivalent. Archives of Dermatology, 134, 293-300

Harris P A; Di Franncesco F; Barisoni D; Leigh I M; Navasaria (1999): Use of hyaluronic acid and cultured autologous keratinocytes and fibroblasts in extensive burns. Lancet, 353, 35-36

Kswai K, Ikarashi Y et al. (1993): Rejection of cultured keratinocyte allografts in persensitized mice. Transplantation 56: 265-269

Lam P K; Chan E S Y; Edward W H et al. (1999): Development and evaluation of a new composite Laserskin graft. J. of Trauma: Injury, Infection and Critical Care, 47; 918-922

Lang E; Schäfer B M; Eickhoff U; Hohl H P; Kramer, M D; Maier-Reif K (1996): Rapid Normalization of epidermal integrin expression after allografting of human keratinocytes. Journal of Investigative Dermatology, 107, 423-427

Leigh I M; Navsaria H; Purkis P E; McKay I (1991): Clinical practice and biological effects of keratinocyte grafting. Annals of the Academy of Medicine, 20 (4)

Lindgren C; Marcusson J A; Toftgard R (1998): Treatment of venous leg ulcers with cryopreserved cultured allogeneic keratinocytes: a prospective open controlled study. British Journal of Dermatology, 139 (2) 271-5.

Maier K (1993): Transplantation von in vitro Epidermis—Chancen and Risiken. Quintessenz 3:289-304

Phillips T J; Gilchrest B A (1989): Cultured allogenic keratinocyte grafts in the management of wound healing: prognostic factors. Journal of Dermatologic Surgery and Oncology, 15 (11)

Reinwald, J G and Green (1975): Serial cultivation of strains of human epidermal keratinocytes: the formation of keratinizing colonies from single cells. Cell 6, 331-344.

Schönfeld M; Moll I; Maier K; Jung E G (1993): Keratinozyten aus der Zellkultur zur Therapie von Hautdefekten. Hautarzt, 44:281-289

Schopp V M; Mirancea N; Fusenig N E. (1999): Epidermal Organization and Differentiation of HaCaT Keratinocytes in Organotypic Coculture with Human dermal Fibroblasts. J. Invest. Dermatology 112. 343-353

Tanczos E; Horch R E; Bannasch H; Andree C; Walgenbach K J; Voigt M; Stark G B (1999): Keratinozytentransplantation and Tissue Engineering. Neue Ansatze in der Behandlung chronischer Wunden. Zentralbl Chir 124 Suppl 1, 81-86

Teepe R G C; Roseeuw D I; Hermans J.; Koebrugge E J; Altena T; De Coninck A; Ponec M; Jan Vermeer B (1993): Randomized trial comparing cryopreserved cultured epidermal allografts with hydrocolloid dressings in healing chronic venous ulcers. Journal of the American Academy of Dermatology, 29/6 (982-988).

Wagner G; Horch R; Debus M; Tanczos E; Jiao X J; Saied S; Stark G. B. (1997): Human keratinocytes cultured subconfluent on esterified hyaluronic acid membranes for resurface full thickness nude mice wounds. European Journal of Cell Biology, 74, No. 47, pp. 61.

The invention claimed is:

1. A process for preserving a preparation of isolated human keratinocytes that are not immortalized and that may be replicated at least 150 times by in vitro cell culture methods, which are cells from the culture KC-BI-1 (DSM ACC 2514) or keratinocytes derived therefrom, wherein said process comprises treating said preparation with a cryoprotectant and then storing said preparation at a temperature of −20° C. to −196° C.

2. A process for preserving a product comprising a carrier which is coated with a preparation of isolated human keratinocytes that are not immortalized and that may be replicated at least 150 times by in vitro cell culture methods, which are cells from the culture KC-BI-1 (DSM ACC 2514) or keratinocytes derived therefrom, wherein the carrier is at least partially colonized with human keratinocytes, wherein said process comprises treating said preparation with a cryoprotectant and then storing said product at a temperature of −20° C. to −196° C.

3. The process according to claim 1 or 2 wherein the preparation or product is treated with a cryoprotectant selected from the group consisting of DMSO, trehalose, glycerol or hydroxyethyl starch.

* * * * *